US00PP30463P3

(12) United States Plant Patent

Klemm et al.

(10) Patent No.: US PP30,463 P3

(45) Date of Patent: Apr. 30, 2019

(54) *PELARGONIUM* PLANT NAMED 'KLEPP17459'

(50) Latin Name: *Pelargonium peltatum*
Varietal Denomination: KLEPP17459

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,930

(22) Filed: May 23, 2018

(65) Prior Publication Data

US 2018/0343777 P1 Nov. 29, 2018

(30) Foreign Application Priority Data

May 24, 2017 (CH) ..... PBR 17-3147

(51) Int. Cl.
*A01H 5/02* (2018.01)
*A01H 6/42* (2018.01)

(52) U.S. Cl.
USPC ..... Plt./332
CPC ..... *A01H 6/425* (2018.05)

(58) Field of Classification Search
USPC ..... Plt./263.1, 332
See application file for complete search history.

*Primary Examiner* — Susan McCormick Ewoldt
*Assistant Examiner* — Karen M Redden
(74) *Attorney, Agent, or Firm* — Bethany R. Roahrig; Cochran Freund & Young LLC

(57) ABSTRACT

A new *pelargonium* plant particularly distinguished by white flowers, early flowering, and a hanging habit, is disclosed.

1 Drawing Sheet

Genus and species: *Pelargonium peltatum.*
Variety denomination: 'KLEPP17459'.

CROSS REFERENCE TO RELATED APPLICATION

The present application claims priority to Switzerland Plant Variety Protection Application No. 17-3147, as filed on May 24, 2017, the entire contents are herein incorporated by reference for all the application teaches and discloses. A European Community Plant Variety Protection Application was filed on May 30, 2017, Application No. 2017/1438.

BACKGROUND OF THE NEW PLANT

The present invention comprises a new and distinct variety of *pelargonium,* botanically known as *Pelargonium peltatum* and hereinafter referred to by the variety name 'KLEPP17459'. 'KLEPP17459' originated from a hand pollination in July 2012 in Stuttgart, Germany between the female proprietary *pelargonium* variety PP-2008-0129 (unpatented) and the male *pelargonium* variety ATLANTIC 'Royal White' (unpatented).

Seeds from the hand pollination were obtained and sown and plants were grown for evaluation. A single plant was selected in June 2013 and subsequently named 'KLEPP17459'. In September 2013 'KLEPP17459' was first vegetatively propagated in Stuttgart, Germany by vegetative cuttings from branches. 'KLEPP17459' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. White flowers;
2. Early flowering; and
3. A hanging habit.

DESCRIPTION OF THE PHOTOGRAPH

This new *pelargonium* plant is illustrated by the accompanying photograph which shows an overall view of the plant. The photograph is of an approximately 10 week old plant old plant grown in Stuttgart, Germany outdoors in July 2015. The colors shown are as true as can be reasonably obtained by conventional photographic procedures.

DESCRIPTION OF THE NEW VARIETY

The following detailed descriptions set forth the distinctive characteristics of 'KLEPP17459'. The data which define these characteristics were collected from asexual reproductions carried out in Stuttgart, Germany. Data was collected on plants grown three months after planting in Stuttgart, Germany under a glass covered greenhouse in April 2018. Color references are to The R.H.S. Colour Chart of The Royal Horticultural Society of London (R.H.S.), 5$^{th}$ edition (2007).

Classification:
*Family.*—Geraniaceae.
*Botanical.—Pelargonium peltatum.*
*Common.—Pelargonium.*
*Designation.—'KLEPP*17459'.

Parentage:
*Female.*—PP-2008-0129 (unpatented).
*Male.*—ATLANTIC 'Royal White' (unpatented).

Plant:
*Form.*—Bushy.
*Habit.*—Hanging.
*Height.*—13.0 cm to 14.0 cm.
*Spread.*—18.0 cm to 22.0 cm.

*Natural flowering season.*—April to October.
*Propagation type.*—Vegetative cuttings.
*Time to produce a finished flowering plant.*—4 months.
*Time to initiate and develop roots.*—4 weeks.
*Root description.*—White, dense, and fine.

Stems:
*Quantity of stems per plant.*—2 to 5.
*Color.*—RHS 144A.
*Surface texture.*—Sparsely pubescent.
*Stem form.*—Round.
*Diameter.*—0.3 cm to 0.5 cm.
*Length.*—7.0 cm to 15.0 cm.
*Internode length.*—2.5 cm to 3.5 cm.
*Anthocyanin.*—Absent.

Leaves:
*Arrangement.*—Alternate.
*Shape.*—Ivy-shaped.
*Apex.*—Acute.
*Base.*—Partly overlapping.
*Margin.*—Entire and lobed.
*Texture* (*both surfaces*).—Sparsely pubescent.
*Length.*—2.5 cm to 5.0 cm.
*Width.*—4.5 cm to 8.5 cm.
*Color.*—Upper surface: RHS 138A. Lower surface: RHS 137C.
*Zonation.*—Absent.
*Petiole.*—Length: 2.0 cm to 4.5 cm. Diameter: 0.2 cm to 0.3 cm. Color: RHS 143B. Strength: Moderate.
*Venation pattern.*—Palmate.
*Venation color.*—Upper surface: RHS 138A. Lower surface: RHS 143C.

Inflorescence:
*Lastingness of flowers on the plant.*—6 to 8 days.
*Umbels.*—Quantity of umbels per plant: 3 to 5. Length: 4.0 cm. Diameter: 8.0 cm.
*Individual florets of the umbel.*—Quantity of florets per umbel: 5 to 10. Depth: 0.7 cm. Diameter: 5.0 cm.
*Fragrance.*—Absent.

Flower buds:
*Cluster shape.*—Round.
*Cluster size.*—Length: 1.5 cm. Width: 1.2 cm.
*Surface texture.*—Moderately pubescent.
*Bud.*—Height: 1.0 cm. Width: 0.5 cm. Shape: Elliptic. Apex: Acute. Base: Obtuse. Margin: Entire. Color: RHS 143A.

Petals:
*Quantity per flower.*—About 20.
*Shape.*—Spatulate.
*Apex.*—Round.
*Base.*—Obtuse.
*Margin.*—Entire.
*Length.*—2.5 cm.
*Width.*—1.2 cm to 1.5 cm.
*Texture* (*both surfaces*).—Smooth.
*Color of lobes.*—Upper lobes: Upper surface: RHS 69D, blushed with RHS N66B. Lower surface: RHS 69D, with veins colored RHS 67B. Lower lobes: Upper surface: RHS 69D. Lower surface: RHS 69D.

Petaloids:
*Quantity per flower.*—5 to 7.
*Shape.*—Mixed.
*Apex.*—Mixed.
*Base.*—Obtuse.
*Margin.*—Entire.
*Length* (*cm*).—1.0 cm to 2.0 cm.
*Width* (*cm*).—0.2 cm to 0.5 cm.
*Surface texture* (*both surfaces*).—Smooth.
*Color* (*both surfaces*).—RHS 69D.

Sepals:
*Number per flower.*—6.
*Shape.*—Elliptic.
*Apex.*—Acute.
*Base.*—Obtuse.
*Margin.*—Entire.
*Surface texture.*—Upper surface: Smooth. Lower surface: Moderately pubescent.
*Color.*—Upper surface: RHS 143B. Lower surface: RHS 143A.
*Length.*—1.5 cm.
*Width.*—0.5 cm.

Pedicel:
*Length.*—2.0 cm.
*Diameter.*—0.2 cm.
*Color.*—RHS 143B and RHS 165A.
*Surface texture.*—Moderately pubescent.
*Strength.*—Moderate.

Peduncle:
*Length.*—7.0 cm.
*Diameter.*—0.3 cm.
*Color.*—RHS 143B.
*Surface texture.*—Moderately pubescent.
*Strength.*—Moderate.

Reproductive organs:
*Stamens.*—Quantity of stamens per flower: 3 to 8. Anther length: 0.4 cm. Filament length: 1.0 cm. Filament color: RHS 69D. Pollen amount: Sparse. Pollen color: RHS 168A.
*Pistils.*—Number: 1. Stigma color: RHS 63B. Style length: 0.4 cm. Style color: RHS 142C. Ovary arrangement: Central. Ovary color: RHS 143A. Ovary diameter: 0.3 cm. Ovary length: 0.5 cm.

Fruit and seed set: None observed.
Disease and pest/insect resistance: None observed.

COMPARISON WITH PARENTAL LINES AND KNOWN VARIETY

'KLEPP17459' is distinguished from its parents as described in Table 1:

TABLE 1

Comparison with Parental Lines

| Characteristic | 'KLEPP17459' | Female PP-2008-0129 | Male ATLANTIC 'Royal White' |
|---|---|---|---|
| Leaf Color | Medium green | Light green | Dark green |
| Vigour | Medium | Strong | Compact |

'KLEPP17459' can be compared to the commercial variety 'Royal White' (patent status unknown). Differences between the two varieties are described in Table 2:

TABLE 2

Comparison with Similar Variety

| Characteristic | 'KLEPP17459' | Commercial line 'Royal White' |
|---|---|---|
| Vigour | Medium | Medium-compact |
| Earliness of flowering | Early | Late |

We claim:

1. A new and distinct variety of *pelargonium* plant named 'KLEPP17459' as illustrated and described herein.

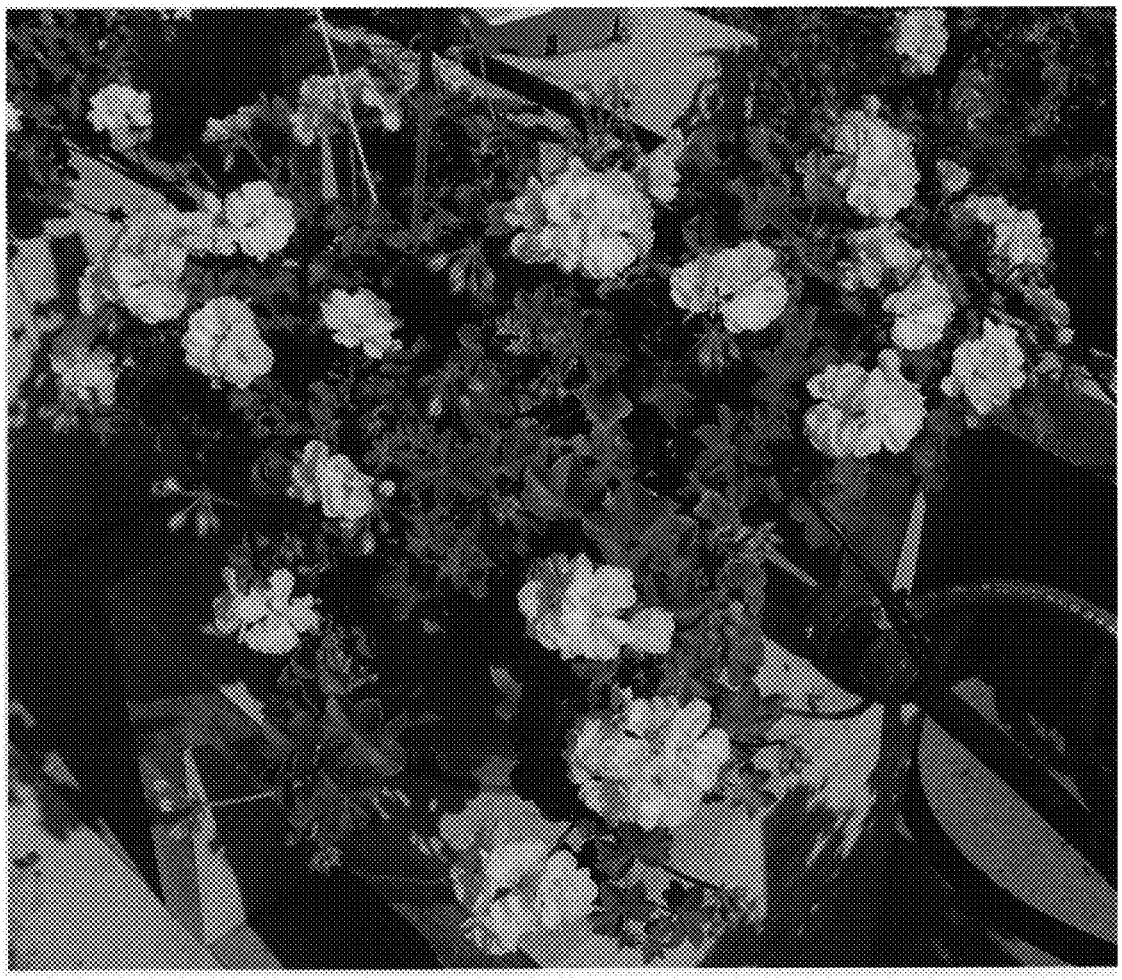

* * * * *